United States Patent [19]

Dobritz

[11] 4,023,587
[45] May 17, 1977

[54] METHOD AND APPARATUS FOR MIXING TWO GASES IN A PREDETERMINED PROPORTION

[75] Inventor: Günther Dobritz, Lubeck, Germany

[73] Assignee: Drägerwerk Aktiengesellschaft, Lubeck, Germany

[22] Filed: May 13, 1976

[21] Appl. No.: 686,658

Related U.S. Application Data

[62] Division of Ser. No. 631,889, Nov. 14, 1975.

[52] U.S. Cl. .................................................. 137/88
[51] Int. Cl.² ....................................... G05D 11/00
[58] Field of Search .................................. 137/7, 88

[56] References Cited

UNITED STATES PATENTS

| | | | |
|---|---|---|---|
| 3,515,155 | 6/1970 | Haffner | 137/7 |
| 3,593,735 | 7/1971 | Reiher | 137/88 |

Primary Examiner—Robert G. Nilson
Attorney, Agent, or Firm—McGlew and Tuttle

[57] ABSTRACT

A method for the control of proportion of two gases which are delivered to a mixed gas line for use for example in a respiratory breathing apparatus in which the gases are delivered to a mixed gas line from a pressure control vessel, comprises continuously monitoring the pressure in the control vessel and when the pressure therein is at an initial predetermined pressure admitting a first gas into the pressure control vessel until the pressure therein increases to a predetermined higher pressure and then stopping the admission of the first gas and initiating the admitting of a second gas into the pressure control vessel, continuing to admit the second gas until a predetermined additional higher pressure is achieved in the pressure control vessel, discontinuing the admission of the second gas when the predetermined additional higher pressure is reached and initiating the withdrawal of the mixed gas through the mixed gas line, continuing to withdraw the mixed gas through the mixed gas line until an initial pressure is again reached in the pressure control vessel at which time the complete process is repeated again. The apparatus includes a first control valve in a first gas supply line to the pressure vessel and a second control valve in a second gas supply line to the pressure control vessel. A third control valve is arranged in a mixed gas delivery line which connects the pressure vessel. All of the three valves are connected by a control device which is responsive to the pressure in the pressure vessel and the individual control valves are set for opening and closing at different control pressures so that the inflow of the first and second gases and the delivery of the mixed gases will be continuously controlled thereby.

4 Claims, 2 Drawing Figures

METHOD AND APPARATUS FOR MIXING TWO GASES IN A PREDETERMINED PROPORTION

This is a division of application Ser. No 631,889 filed Nov. 14, 1975.

BACKGROUND OF THE INVENTION

1. Field of the Invention

This invention relates in general to a method and apparatus for mixing two gases in a predetermined proportion and in particular to a new and useful apparatus and method for continuously supplying a gas mixture from two separate gas supplies.

2. Description of the Prior Art

There is a known device for controlling the gas mixture of different kinds of gases in which each gas is expanded separately through a two-stage pressure reducer to a uniform pressure and then each gas is discharged through a respective adjustable metering nozzle controlling the proportion in the gas mixture into the mixer tube. In order to obtain a uniform final pressure after the pressure reducers, the pressure reducers are provided with an auxiliary control which receives control impulses from the uniform final pressure. The uniform final pressure may be maintained by means of an equalizing controller which acts on the control pressure of the pressure reducers. This has the effect that upon occurrence of a pressure difference in the gas lines bewteen the pressure reducers and the metering nozzles at the side of the higher pressure, the control pressure drops and a smaller gas volume is delivered. At the other side the control pressure of the other pressure reducer increases so that a larger volume of gas is delivered. In this manner, an equalized low pressure is produced which is a supply condition for the metering nozzles. This known device has the disadvantage that even at an equalized supply pressure, the rate of flow through the metering nozzles depends on the pressure in the mixing tube. In addition the unequal inside diameters of the nozzles must be considered. In this respect the rate of flow depends on the pressure ratio. Thus the rate of flow and therefore the proportion of the mixture depends on two factors which are not easily controllable. Consequently such a device is unsuitable for apparatus in which the pressure differences can occur in the mixer tube. This disadvantage is of importance particularly in medical devices where for example if narcotics are admixed to a breathing gas there is a need for an exact proportion to be observed.

In another known method of mixing two gases in a predetermined proportion, the gases to be mixed are supplied through pressure governors which for adjusting the pressure ratio are coupled to each other. The outlet pressures of the pressure governors are arranged in an adjustable predetermined ratio to each other. Each gas flows at its own pressure into a respective chamber having a predetermined or adjustable volume. After the filling and interruption of the gas supply by a switch over valve, the gas flows into the gas outlet line through a further pair of pressure governors which are adjusted to the same pressure ratio as the first pressure governors. With such a method a gas mixture is produced which has a definite concentration since a definite gas quantity is mearsured off each gas to be mixed. These quantities after discharge mix with each other in accordance with the metered quantitative proportion. Concentration variations do not occur, not even at variations of the gas pressure in the connected operated device. To obtain this result however a relatively complicated arrangement is necessary, primarily because of the requirement for two pairs of pressure governors.

SUMMARY OF THE INVENTION

The present invention provides a method in a device of simple design which makes it possible to vary the mixing proportions of two gases to any desired extent with the aid of simple means and preferably with the use of an electric control signal. In addition the device has to switch automatically normal operating conditions to conditions which are safe for the user and at the same time it must signal such a disturbance.

In accordance with the invention a method is provided in which a first gas such as a gas A controlled by a first control valve which opens at a predetermined initial pressure $P_1$ and closes at a predetermined actuating pressure $P_2$ is admixed with a second gas. The second gas a gas B controlled by a second control valve which opens at an actuating pressure $P_2$ and closes at a predetermined final pressure $P_3$ is supplied to a pressure vessel along with the first gas and the gas mixture after having reached the final pressure $P_3$ is discharged from the vessel through a third control valve which opens at a final pressure $P_3$ and closes upon reestablishment of the initial pressure $P_1$.

The advantages obtained with the apparatus and method include the fact that only a single parameter that is the respective actuating pressure $P_2$ has to be varied in order to produce the desired gas mixture. In view of the fact that the pressure meters which are available commercially are very accurate it is easy to provide for a control based entirely on pressure changes. The mixing of the gases is effected merely by varying the actuating pressure for opening and closing the various valves which are necessary. The value of this actuating pressure $P_2$ which is intermediate two definite pressures that is an initial pressure $P_1$ and a final pressure $P_3$ is a determining pressure for the proportion of gases $A$ and $B$ in a mixture in accordance with the equation $P_2 = P_1 + (P_3 - P_1) \times A\%$ divided by 100; where $A$ is the desired proportion of gas A and the proportion of gas $B$ in the mixture is $B\% = 100\% - A\%$.

Since after the first adjustment $P_1$ and $P_3$ are constant the determination of the actuating pressure $P_2$ is very simple. A gas mixing apparatus in accordance with the present method would be equipped with a correspondingly ranging adjusting device.

A gas mixing device for carrying out the inventive method is very simple in design and sonce only a single pressure is to be varied for varying the gas proportion in the mixed gas, is free from problems of operation. For conveying the gases in the gases mixing device, only a few component parts are needed which form an operational unit insofar as the supply lines for the gases A and B are concerned. The construction includes a first and second supply line connected into a pressure vessel each having its associated first and second control valve and a delivery line which extends outwardly from the pressure vessel for supplying the mixed gas which has its own control valve. In addition a supply reservoir may be connected to the mixed gas line.

The control valves are advantageously designed as solenoid valves which are coupled through a pneumatic electrotransducer to a pressure meter provided on the pressure vessel. The first control valve in the first gas supply line is advantageously adjusted for opening to an initial pressure $P_1$ and for closing it operates at an actuating pressure $P_2$. The second control valve and the second gas supply line is adjusted for example to open to an actuating pressure $P_2$ and to close at a final pressure $P_3$. Third control valve is adjusted for opening at a final pressure $P_3$ and for closing the initial pressure $P_1$.

Particular advantages of the invention result from the possibility of equipping the control valve with a control device which starts with the opening of the second control valve and is stopped with the closing and, upon exceeding the normal time up to the closure, releases a switch pulse and starts an alarm. This would make it possible to use the gas mixing device in breathing apparatus and medical devices. For such apparatus and devices it is essential that any undesirable operational conditions will not lead to dangerous consequences to the patient. For example in the medical technique preferably compressed air is mixed with oxygen and laughing gas is mixed with oxygen. While air is mixed with oxygen upon a supply interruption of one of these gases the other gas has to continue to flow to the patient. However not only the cases to be considered in which as just mentioned both gases are breathable but also the possibility that one of the gases is breathable and the other gas may be even dangerous. In the first case thus with a breathable gas both control valves for gases A and B are equipped with a control device by which upon interruption of the supply of one of the gases the control valve of the other gas is automatically switched to the entire pressure range form $P_1$ to $P_3$ so that then during the whole filling phase the single gas will be continued to be supplied to the pressure vessel.

In contrast thereto if one of the gases is breathable and the other is not, the control valve is equipped with c control device for the non-breathable gas. Such a control device would effect a switching of the breathable gas to the breathable gas to the full operation in the event of disruption of the non-breathable gas but it would switch off the device in the event of the cutout of the breathable gas so that the non-breathable gas would not be supplied alone. Simultaneously at the occurrence of this condition an alarm is started and this is of vital importance.

In another embodiment of the invention the pressure vessel may be connected to a switch-over valve which permits either inflow of the mixed gas into the pressure vessel or the outflow of the mixed gas to a mixed gas to a mixed gas supply line. In addition the two supply lines for the gas may be connected through a switch-over valve to a single supply line to the pressure vessel which is connected to the first switch-over valve.

Accordingly it is an object of the invention to provide a method for the control of the proportion of two gases which are delivered to a mixed gas line from a pressure control vessel which comprises continuously monitoring the pressure in the control vessel and when the pressure therein is at an initial predetermined pressure admitting a first gas into the pressure control vessel until the pressure in the vessel increases to a predetermined higher pressure and then stopping the admission of the first gas and initiating the admission of a second gas into the pressure control vessel, continuing to admit the second gas until a predetermined additional higher pressure is reached and then stopping the admission of the second gas and beginning the withdrawal of the mixed gases from the pressure vessel to the mixed gas line, and continuing to withdraw the mixed gases until the pressure in the pressure vessel returns to the initial predetermined pressure and repeating the procedure.

A futher object of the invention is to provide an apparatus for mixing two gases in a predetermined proportion which comprises a pressure control vessel with a first connecting line for the supply of a first gas having a first valve therein and a second connecting line for a supply of a second gas having a second control valve therein and with a third mixed gas control valve in a mixed gas line connected to the pressure control vessel wherein each of the first, second and third valves are set to operate for opening and closing at distinct different pressures and which includes a transducer connected to the pressure vessel to monitor the pressure and to effect the pressure control opening and closing of the first, second and third valves in accordance with their set values of pressure for opening and closing.

A further object of the invention is to provide a device for mixing two gases in a predetermined portion which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

GENERAL DESCRIPTION OF THE PREFERRED EMBODIMENTS

Figure 1:
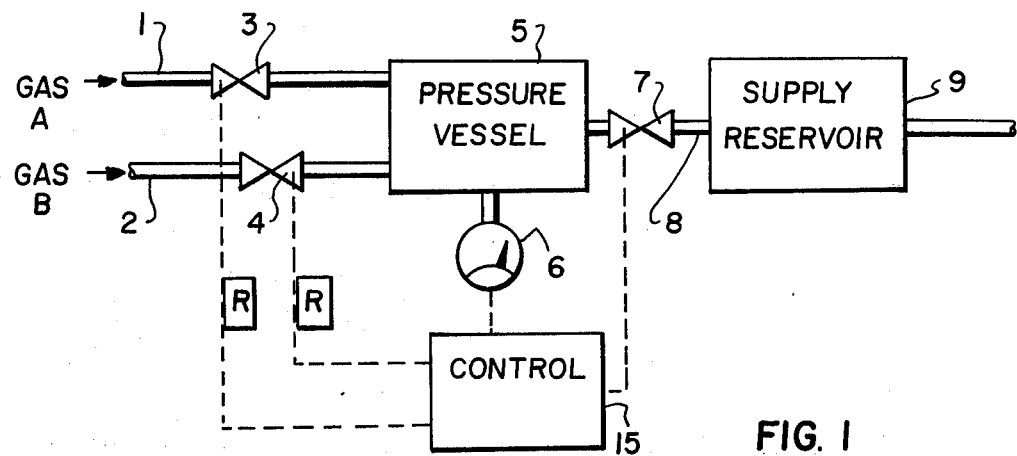
FIG. 1 is a diagrammatical view of a gas mixing device constructed in accordance with the invention.

Referring to the drawings in particular the invention embodied therein in FIG. 1 comprises an apparatus for mixing two gases in a predetermined proportion and it includes a gas supply line 1 for a first gas A and a gas supply line 2 for a second gas B which are connected through a first control valve 3 and a second control valve 4 respectively to a pressure vessel 5. The pressure in the pressure vessel 5 is measured by a meter 6 variations of pressure are employed for producing a control of each of the second valve 3 and 4 and a third discharge valve 7 in a mixed gas line 8 and using a control device such as a transducer 15. The mixed gas line may be connected for supplying the mixed gas directly to its place of use or it may be delivered to a supply reservoir 9 as indicated in FIG. 1.

An example of the operation of the device is as follows:

An initial pressure in the vessel 5 may be said for example to be a pressure $P_1$ of two bars. Under this pressure the control device 15 actuates the first control valve 1 so that it opens. The first gas A then flows through the supply line 1 into the pressure vessel 5. The gas A continues to flow into the pressure vessel 5 until the pressure in the vessel increases to an actuating pressure $P_2$ which is a predetermined pressure which may for example be 2.7 bars. This actuating pressure $P_2$ acts through the control device 15 to close the first control valve 3 and to open the second control valve 4.

The first gas A stops flowing and the gas B then flows in through the supply line 2 and the control valve 4 into the pressure vessel 5. This causes the pressure in the pressure vessel 5 to increase until a predetermined additional pressure a pressure $P_3$ is reached which for example may be 3 bars. At the additional pressure value the second control valve 4 will be closed by the control mechanism 15 and a third control valve 7 will be opened at this additional pressure $P_3$. Therefore the mixed gas will flow out of the pressure vessel 5 through the third valve and either into the supply reservoir 9 or directly through the mixed gas line 8 to the place of use. With this discharge the pressure in the pressure vessel 5 will decrease again until it arrives at the initial pressure $P_1$. Thereupon the third control valve 7 is set to be closed by the control 15 and the first control valve 3 will be reopened. At this stage the next cycle is started and then repeated.

The proportion of gases A and B in the mixed gas follows the actuating pressure $P_2$. In the present example, the mixed gas contains 70% of gas A and 30% of gas B. These percentages result from the adjusted actuating pressure $P_2 = 2.7$ bars, the initial pressure $P_1 = 2$ bars and the final pressure $P_3 = 3$ bars.

Since $P_2$ can be varied within the range of $P_1$ to $P_3$ the proportion of the gases can be adjusted from zero to 100% of the mixed gas.

Figure 2:
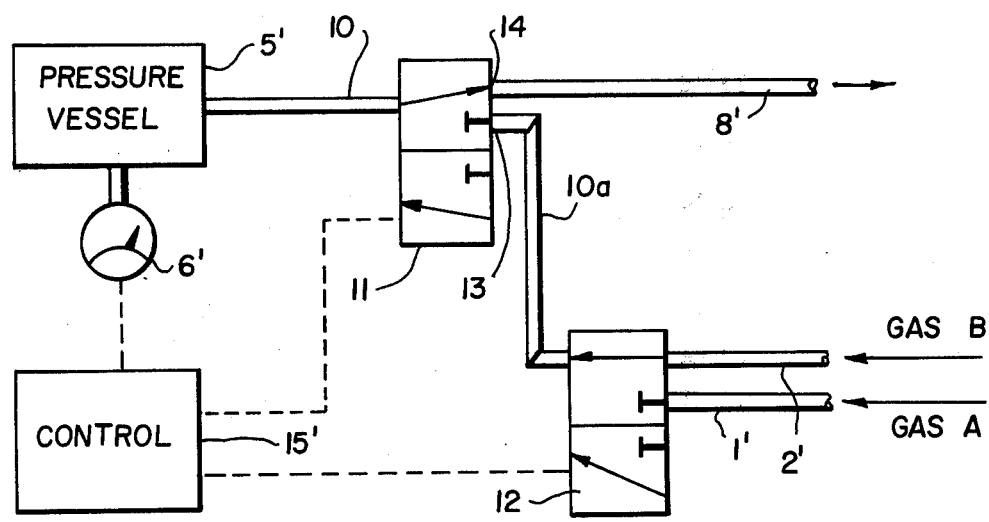
FIG. 2 is a view similar to FIG. 1 of another embodiment of the invention.

The embodiment of the invention shown in FIG. 2 is similar to that of FIG. 1 and similar parts are similarly designated but with a prime. In this embodiment the control valves which are employed include a single switch-over valve 11 which is connected through a line 10 to the pressure vessel 5' and a line 10a to the selected connection of the supply connections 1' and 2'. In addition the switch valve 11 is also connected to a mixed gas line or supply 8'. The valve 12 permits a switch-over from the supply lines 1' or 2' for the gases A and B to feed one or the other through the connecting line 10a to the switch valve 11.

In the embodiment of FIG. 2 at an initial pressure $P_1$ gas A flows to the pressure vessel 5 to the switch-over valve 12 which is switched to the supply line 1 and through a switch-over valve 11 which is switched to the inlet 13 connecting the connecting line 10a. When the pressure $P_2$ is reached in the vessel 5' the switch-over valve 12 is operated to the position in which gas B from the supply line 2 can flow through the connecting line 10a in the switch-over valve 11 remains in an unchanged position so that the gas B can flow into the pressure vessel 5'. a soon as the pressure $P_3$ is attained the switch-over valve 11 switched to the outlet 14 leading to the mixed gas line 8'. The mixed gas is then discharged. Thereupon the pressure is reduced to an initial pressure $P_1$, the switch-over valve 11 switches again to the inlet 13 and switch-over valve 12 switches to supply line 1 and thereby to gas A.

While specific embodiments of the invention have been shown and described in detail to illustrate the application of the principles of the invention, it will be understood that the invention may be embodied otherwise without departing from such principles.

Each of the circuits connected to the first control valve 3 and the second control valve 4 in the embodiment of FIG. 1 is advantageously provided with an alarm device R which becomes actuated when either of the valves 3 or 4 fail to switch when a given pressure condition is effected in the pressure vessel.

What is claimed is:

1. An apparatus for mixing two gases in a predetermined proportion, comprising a pressure control vessel, a first line for supplying a first gas connected to said pressure control vessel, a first gas control valve in said first connecting line, a second connecting line for the supply of a second gas connected to said pressure control vessel, a second gas control valve in said connecting line, a mixed gas line for delivering the mixed gas connected to said pressure control vessel, a third gas control valve in said mixed gas line, each of said first, second and third control valves being set for opening and closing at separate distinct pressures, and control means connected to said pressure vessel and to each of said first, second and third valves to open and close said valves in accordance with the set values of pressure for opening and closing, said valves being set so that an initial pressure in said pressure control vessel causes the opening of said first valve to permit inflow of a first gas through said first gas connecting line to said pressure control vessel, said second valve being set to open and said first valve being set to close upon the increase of the pressure in said pressure control vessel to a higher pressure above said initial pressure, said second valve being set to close and said third valve being set to open when a predetermined additional higher pressure has been reached in said pressure control vessel, said third valve being set to close and said first valve being set to open once again when said initial pressure returns to said pressure control vessel.

2. A device according to claim 1, including an alarm connected to each of said first and second valves and to said control means which is operable on failure of said first and second valves to switch in response to said control means.

3. An apparatus according to claim 1, wherein said first and second valves comprise a switch-over valve, said first and second connecting lines including first and second supply lines connected to said switch-over valve and a single line connected from said switch-over valve to said pressure vessel, said thrid valve comprising a switch-over valve, said third line including a connection between said pressure valve and said second switch-over valve and a connection from said second switch-over valve forming a mixing gas line, said connection from said first switching valve to said pressure valve including a connection from said first switching valve to said second switching valve and said connection of said second switching valve to said pressure vessel.

4. A device according to claim 3, wherein said first switchover valve switches at the initial pressure to the first supply line and at an actuating pressure to the second supply line and said second switchover valve switches at an initial pressure to the connection between said first and second switchover valves and at a final pressure to connect said pressure vessel to said mixing gas line.

* * * * *